(12) United States Patent
Pham et al.

(10) Patent No.: US 7,803,283 B2
(45) Date of Patent: Sep. 28, 2010

(54) AZEOTROPE-LIKE COMPOSITIONS OF 2-CHLORO-3,3,3-TRIFLUOROPROPENE (HCFC-1233XF) AND 2-CHLORO-1,1,1,2-TETRAFLUOROPROPANE (HCFC-244BB)

(75) Inventors: Hang T. Pham, Amherst, NY (US); Rajiv R. Singh, Getzville, NY (US); Hsuehsung Tung, Getzville, NY (US); Konstantin A. Pokrovski, Orchard Park, NY (US); Daniel C. Merkel, West Seneca, NY (US)

(73) Assignee: Honeywell Internationl Inc., Morristown, NJ (US)

( * ) Notice: Subject to any disclaimer, the term of this patent is extended or adjusted under 35 U.S.C. 154(b) by 28 days.

(21) Appl. No.: 12/405,347

(22) Filed: Mar. 17, 2009

(65) Prior Publication Data

US 2009/0242832 A1    Oct. 1, 2009

Related U.S. Application Data

(60) Provisional application No. 61/040,759, filed on Mar. 31, 2008.

(51) Int. Cl.
*C09K 5/04* (2006.01)
(52) U.S. Cl. .......................................... 252/67; 203/67
(58) Field of Classification Search .................. 252/67; 203/67
See application file for complete search history.

(56) References Cited

U.S. PATENT DOCUMENTS

| 2007/0007488 | A1 | 1/2007 | Singh et al. .................... 252/68 |
| 2007/0197842 | A1 | 8/2007 | Mukhopadhyay et al. ... 570/155 |
| 2009/0030247 | A1 | 1/2009 | Johnson et al. ............. 571/155 |
| 2009/0043137 | A1 | 2/2009 | Tung et al. |

FOREIGN PATENT DOCUMENTS

| EP | 2107048 | * 10/2009 |
| WO | WO2007/079431 | 7/2007 |
| WO | WO2008/054782 | 5/2008 |
| WO | WO2009/003084 | 12/2008 |
| WO | WO2009/009421 | 1/2009 |

OTHER PUBLICATIONS

U.S. Appl. No. 61/091,034, filed Aug. 22, 2008.
U.S. Appl. No. 61/087,206, filed Aug. 8, 2008.
U.S. Appl. No. 12/179,055, filed Jul. 24, 2008.
U.S. Appl. No. 61/073,186, filed Jun. 17, 2008.
U.S. Appl. No. 61/053,518, filed May 15, 2008.
U.S. Appl. No. 61/047,613, filed Apr. 24, 2008.
U.S. Appl. No. 61/043,451, filed Apr. 9, 2008.
U.S. Appl. No. 61/020,390, filed Jan. 10, 2008.

* cited by examiner

*Primary Examiner*—John R Hardee
(74) *Attorney, Agent, or Firm*—Bruce Bradford

(57) ABSTRACT

Provided are azeotropic and azeotrope-like compositions of 2-chloro-3,3,3-trifluoropropene (HCFO-1233xf) and 2-chloro-1,1,1,2-tetrafluoropropane (HCFC-244bb). Such azeotropic and azeotrope-like compositions are useful as intermediates in the production of 2,3,3,3-tetrafluoropropene (HFO-1234yf).

28 Claims, No Drawings

AZEOTROPE-LIKE COMPOSITIONS OF 2-CHLORO-3,3,3-TRIFLUOROPROPENE (HCFC-1233XF) AND 2-CHLORO-1,1,1,2-TETRAFLUOROPROPANE (HCFC-244BB)

CROSS REFERENCE TO RELATED APPLICATION

This application claims the benefit of U.S. Provisional patent application Ser. No. 61/040,759 filed Mar. 31, 2008 which is incorporated herein by reference.

BACKGROUND OF THE INVENTION

1. Field of the Invention

The present invention provides azeotrope-like compositions of 2-chloro-3,3,3-trifluoropropene (HCFO-1233xf) with 2-chloro-1,1,1,2-tetrafluoropropane (HCFC-244bb); and uses thereof, and in process for separating the azeotrope-like mixtures. More particularly the invention pertains to such azeotropic and azeotrope-like compositions which are useful as intermediates in the production of 2,3,3,3-tetrafluoropropene (HFO-1234yf).

2. Description of the Related Art

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the Earth's ozone layer. Therefore, stratospherically safer alternatives to these materials are desirable. Consequently, there is a worldwide effort to use fluorine-substituted hydrocarbons which contain fewer or no chlorine substituents. In this regard, 2-chloro-3,3,3-trifluoropropene (HCFO-1233xf) and 2-chloro-1,1,1,2-tetrafluoropropane (HCFC-244bb), having low ozone depletion potential, are being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HCFO-1233xf and HCFC-244bb are intermediates in the production of 2,3,3,3-tetrafluoropropene (HFO-1234yf) which is well known in the art as described in U.S. Applications 20070007488 and 20070197842, the specifications of which are incorporated herein by reference. HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

It has now been found that an important intermediate in the production of substantially pure HFO-1234yf, is an azeotropic or azeotrope-like composition of 2-chloro-3,3,3-trifluoropropene (HCFO-1233xf) and 2-chloro-1,1,1,2-tetrafluoropropane (HCFC-244bb). This intermediate, once formed, may thereafter be separated into its component parts by known in the art techniques. The azeotropic and azeotrope-like compositions find use not only as intermediates in the production of HFO-1234yf, but they also exhibit properties that make that make them advantageous for use as, or in, a refrigerant, an aerosol, and blowing agent compositions. In addition, the formation of an azeotropic or azeotrope-like composition of HCFC-1232xf and HCFC-244bb is useful in separating a mixture of HCFC-1232xf/HCFC-244bb and an impurity such as a halocarbon, for example, 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane; or 1,2-dichloro-3,3,3-trifluoropropene. When it is desired to separate a mixture of HCFO-1233xf and an impurity, HCFC-244bb is added to form an azeotropic mixture of HCFO-1233xf and HCFC-244bb, and then the impurity is removed from the azeotropic mixture, such as by distillation or other known means. Likewise, when it is desired to separate a mixture of HCFC-244bb and an impurity, HCFO-1233xf is added to form an azeotropic mixture of HCFC-244bb and HCFO-1233xf, and then the impurity is removed from the azeotropic mixture, such as by distillation or other known means. This binary azeotrope or azeotrope-like composition is then available for separation into its component parts.

SUMMARY OF THE INVENTION

The invention provides an azeotropic or azeotrope-like composition consisting essentially of 2-chloro-1,1,1,2-tetrafluoropropane and 2-chloro-3,3,3-trifluoropropene.

The invention further provides a method of forming an azeotropic or azeotrope-like composition which comprises forming a blend consisting essentially of from about 1 to about 25 weight percent 2-chloro-1,1,1,2-tetrafluoropropane and from about 75 to about 99 weight percent 2-chloro-3,3,3-trifluoropropene to thereby form an azeotropic or azeotrope-like composition having a boiling point of from about 0° C. to about 60° C. at a pressure of from about 9 psia to about 65 psia.

The invention also provides a method for removing 2-chloro-3,3,3-trifluoropropene from a mixture containing 2-chloro-3,3,3-trifluoropropene and at least one impurity, which comprises adding 2-chloro-1,1,1,2-tetrafluoropropane to the mixture in an amount sufficient to form an azeotropic or azeotrope-like composition of the 2-chloro-3,3,3-trifluoropropene and the 2-chloro-1,1,1,2-tetrafluoropropane, and thereafter separating the azeotropic composition from the impurity.

The invention also provides a method for removing 2-chloro-1,1,1,2-tetrafluoropropane from a mixture containing 2-chloro-1,1,1,2-tetrafluoropropane and at least one impurity, which comprises adding 2-chloro-3,3,3-trifluoropropene to the mixture in an amount sufficient to form an azeotropic or azeotrope-like composition of the 2-chloro-1,1,1,2-tetrafluoropropane and the 2-chloro-3,3,3-trifluoropropene, and thereafter separating the azeotropic composition from the impurity.

DETAILED DESCRIPTION OF THE INVENTION

In a method of preparing a HCFC-244bb precursor, reagents are fluorinated with hydrogen fluoride. This may be done, for example, by the liquid phase or gas phase catalytic fluorination of $CF_3CCl=CH_2$ (HCFO-1233xf) with HF to yield HCFC-244bb. The reaction products of such precursors include HCFC-244bb, unreacted HCFO-1233xf, unreacted HF and other by-products. Upon removal of the by-products and HF, a binary azeotrope or azeotrope-like composition of HCFC-244bb and HCFO-1233xf is formed. This binary azeotrope or azeotrope-like composition is then available for separation into its component parts. The azeotropic or azeotrope-like compositions of the HCFC-244bb and HCFO-1233xf are also useful as recycle to the fluorination reactor. Thus, for example, in a process for producing HCFC-244bb, one can recover a portion of the unreacted HCFO-1233xf as an azeotropic or azeotrope-like composition of HCFC-244bb and HCFO-1233xf and then recycle the composition to the reactor for further fluorination.

In a method of preparing HCFO-1233xf and HCFC-244bb precursors, reagents are fluorinated with hydrogen fluoride. This may be done, for example, by the gas phase catalytic fluorination of $CCl_2=CClCH_2Cl$ with HF to yield HCFO-1233xf. Such methods are disclosed in U.S. Application 20070197842, the specification of which is incorporated herein by reference. The reaction products of such precursors include HCFO-1233xf, unreacted HF and other by-products.

HCFO-1233xf forms azeotropic and azeotrope-like mixtures with HCFC-244bb. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of HCFC-244bb and HCFO-1233xf to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only HCFC-244bb with HCFO-1233xf.

In a preferred embodiment, the inventive composition contains from about 1 to about 25 weight percent HCFC-244bb, preferably from about 1.5 weight percent to about 15 weight percent and most preferably from about 2 weight percent to about 10 weight percent based on the weight of the azeotropic or azeotrope-like composition.

In a preferred embodiment, the inventive composition contains from about 75 to about 99 weight percent HCFO-1233xf, preferably from about 85 weight percent to about 98.5 weight percent and most preferably from about 90 weight percent to about 98 weight percent based on the weight of the azeotropic or azeotrope-like composition.

The composition of the present invention preferably has a boiling point of about from about 0° C. to about 60° C. at a pressure of from about 9 psia to about 65 psia. In one embodiment it has a boiling point of about 0° C. at a pressure of about 9 psia. In another embodiment it has a boiling point of about 25° C. at a pressure of about 24 psia. In another embodiment it has a boiling point of about 60° C. at a pressure of about 65 psia. An azeotropic or azeotrope-like composition having about 6±4 weight percent HCFC-244bb and about 94±4 weight percent HCFO-1233xf was found at about 10° C.

In another embodiment of the invention, 2-chloro-3,3,3-trifluoropropene (HCFO-1233xf) may be removed from a mixture containing 2-chloro-3,3,3-trifluoropropene (HCFO-1233xf) and an impurity which may, for example, result from manufacturing steps in the preparation of 2-chloro-3,3,3-trifluoropropene (HCFO-1233xf). This is done by adding 2-chloro-1,1,1,2-tetrafluoropropane (HCFC-244bb) to the mixture of the 2-chloro-3,3,3-trifluoropropene (HCFO-1233xf) and impurity. 2-chloro-1,1,1,2-tetrafluoropropane (HCFC-244bb) is added to the mixture in an amount sufficient to form an azeotropic composition of the 2-chloro-3,3,3-trifluoropropene (HCFO-1233xf) and the 2-chloro-1,1,1,2-tetrafluoropropane (HCFC-244bb), and thereafter the azeotropic composition is separated from the impurity, for example by distillation or other art recognized separating means. In one embodiment, the impurity itself does not form an azeotropic mixture with 2-chloro-3,3,3-trifluoropropene (HCFO-1233xf), 2-chloro-1,1,1,2-tetrafluoropropane (HCFC-244bb), or a mixture of 2-chloro-3,3,3-trifluoropropene (HCFO-1233xf) and 2-chloro-1,1,1,2-tetrafluoropropane (HCFC-244bb). In another embodiment, the impurity does form an azeotropic mixture with 2-chloro-3,3,3-trifluoropropene (HCFO-1233xf), 2-chloro-1,1,1,2-tetrafluoropropane (HCFC-244bb), or a mixture of 2-chloro-3,3,3-trifluoropropene (HCFO-1233xf) and 2-chloro-1,1,1,2-tetrafluoropropane (HCFC-244bb).

In another embodiment of the invention, 2-chloro-1,1,1,2-tetrafluoropropane (HCFC-244bb) may be removed from a mixture containing 2-chloro-1,1,1,2-tetrafluoropropane (HCFC-244bb) and an impurity which may, for example, result from manufacturing steps in the preparation of 2-chloro-1,1,1,2-tetrafluoropropane. (HCFC-244bb). This is done by adding 2-chloro-3,3,3-trifluoropropene (HCFO-1233xf) to the mixture of the 2-chloro-1,1,1,2-tetrafluoropropane. (HCFC-244bb) and impurity. 2-chloro-3,3,3-trifluoropropene (HCFO-1233xf) is added to the mixture in an amount sufficient to form an azeotropic composition of the 2-chloro-1,1,1,2-tetrafluoropropane. (HCFC-244bb) and the 2-chloro-3,3,3-trifluoropropene (HCFO-1233xf), and thereafter the azeotropic composition is separated from the impurity, for example by distillation or other art recognized separating means. In one embodiment, the impurity itself does not form an azeotropic mixture with 2-chloro-1,1,1,2-tetrafluoropropane (HCFC-244bb), 2-chloro-3,3,3-trifluoropropene (HCFO-1233xf), or a mixture of 2-chloro-1,1,1,2-tetrafluoropropane (HCFC-244bb) and 2-chloro-3,3,3-trifluoropropene (HCFO-1233xf). In another embodiment, the impurity does form an azeotropic mixture with 2-chloro-1,1,1,2-tetrafluoropropane (HCFC-244bb), 2-chloro-3,3,3-trifluoropropene (HCFO-1233xf), or a mixture of 2-chloro-1,1,1,2-tetrafluoropropane (HCFC-244bb) and 2-chloro-3,3,3-trifluoropropene (HCFO-1233xf). In another embodiment, one may separate 2-chloro-1,1,1,2-tetrafluoropropane from an azeotropic or azeotrope-like composition of 2-chloro-1,1,1,2-tetrafluoropropane and 2-chloro-3,3,3-trifluoropropene using pressure swing distillation.

Typical impurities of 2-chloro-3,3,3-trifluoropropene (HCFO-1233xf) and 2-chloro-1,1,1,2-tetrafluoropropane (HCFC-244bb) include other halocarbons which may be miscible with 2-chloro-3,3,3-trifluoropropene (HCFO-1233xf) and 2-chloro-1,1,1,2-tetrafluoropropane (HCFC-244bb) such as 1,1,1,2,3-pentachloropropane; 1,1,2,3-tetrachloropropene; 2,3,3,3-tetrafluoropropene; 2,3-dichloro-3,3-difluoropropene (1232xf); 1,1,1,2,2-pentafluoropropane; 2,3,3,3-tetrafluoropropene or 1,2-dichloro-3,3,3-trifluoropropene.

The following non-limiting examples serve to illustrate the invention.

EXAMPLE 1

An ebulliometer comprising a vacuum jacketed tube with a condenser on top which is further equipped with a Quartz Thermometer is used. About 20.91 g 1233xf is charged to the ebulliometer and then 244bb is added in small, measured increments. Temperature depression is observed when HCFC-244bb is added to HCFO-1233xf, indicating a binary minimum boiling azeotrope is formed. From greater than about 0 to about 5 weight percent 244bb, the boiling point of the composition stays below or around the boiling point of 1233xf. The boiling temperature of HCFO-1233xf (98% pure) is about 9.82° C. at 14.4 psia, and the boiling of TOX grade HCFO-1233xf (99.99% pure) is about 12° C. at 14.5 psia. The boiling point of HCFC-244bb is about 14.0 at 14.5 psia. The binary mixtures shown in Table 1 were studied. The compositions exhibit azeotrope and/or azeotrope-like properties over this range.

TABLE 1

HCFO-1233xf/HCFC-244bb Compositions at P = 14.4 psia.

| T (° C.) | Wt. % HCFO-1233xf | Wt. % HCFC-244bb |
| --- | --- | --- |
| 9.82 | 100.0 | 0.0 |
| 9.80 | 99.38 | 0.62 |
| 9.79 | 98.35 | 1.65 |
| 9.78 | 96.54 | 3.46 |
| 9.78 | 94.83 | 5.17 |
| 9.85 | 93.18 | 6.82 |
| 9.95 | 91.11 | 8.89 |
| 10.00 | 87.45 | 12.45 |
| 10.25 | 83.91 | 16.09 |
| 10.36 | 80.86 | 19.14 |
| 10.43 | 76.37 | 23.63 |

EXAMPLE 2

The vapor pressure of pure HCFO-1233xf, HCFC-244bb and 50/50% mixture of HCFO-1233xf/HCFC-244bb was measured. The result in Table 2 shows that the vapor pressure of this mixture is higher than the vapor pressure of either pure component HCFO-1233xf, and HCFC-244bb at 0, 25 and 60° C.

TABLE 2

Vapor Pressure of HCFO-1233xf/HCFC-244bb mixture

| T (° C.) | Pressure (Psia) | Wt. % HCFO-1233xf/ HCFC-244bb |
| --- | --- | --- |
| 0.0 | 8.87 | 100.0/0.0 |
|  | 9.43 | 50.0/50.0 |
|  | 8.24 | 0.0/100.0 |
| 25.0 | 22.88 | 100.0/0.0 |
|  | 23.81 | 50.0/50.0 |
|  | 21.33 | 0.0/100.0 |
| 60.0 | 64.58 | 100.0/0.0 |
|  | 64.98 | 50.0/50.0 |
|  | 59.75 | 0.0/100.0 |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. An azeotropic or azeotrope-like composition consisting essentially of 2-chloro-1,1,1,2-tetrafluoropropane and 2-chloro-3,3,3-trifluoropropene.

2. An azeotropic or azeotrope-like composition which consists essentially of from about 1 to about 25 weight percent 2-chloro-1,1,1,2-tetrafluoropropane and from about 75 to about 99 weight percent 2-chloro-3,3,3-trifluoropropene, which composition has a boiling point of from about 0° C. to about 60° C. at a pressure of from about 9 psia to about 65 psia.

3. The composition of claim 2 which consists of 2-chloro-1,1,1,2-tetrafluoropropane and 2-chloro-3,3,3-trifluoropropene.

4. The composition of claim 2 wherein the 2-chloro-1,1,1,2-tetrafluoropropane is present in the amount from about 1 to about 25 weight percent.

5. The composition of claim 2 wherein the 2-chloro-3,3,3-trifluoropropene is present in the amount from about 75 to about 99 weight percent.

6. The composition of claim 2 having a boiling point of about 0° C. at a pressure of about 9 psia; or a boiling point of about 25° C. at a pressure of about 24 psia; or a boiling point of about 60° C. at a pressure of about 65 psia.

7. A method of forming an azeotropic or azeotrope-like composition which comprises forming a blend consisting essentially of from about 1 to about 25 weight percent 2-chloro-1,1,1,2-tetrafluoropropane and from about 75 to about 99 weight percent 2-chloro-3,3,3-trifluoropropene to thereby form an azeotropic or azeotrope-like composition having a boiling point of from about 0° C. to about 60° C. at a pressure of from about 9 psia to about 65 psia.

8. The method of claim 7 further comprising the step of separating 2-chloro-1,1,1,2-tetrafluoropropane from an azeotropic or azeotrope-like composition of 2-chloro-1,1,1,2-tetrafluoropropane and 2-chloro-3,3,3-trifluoropropene by pressure swing distillation.

9. The method of claim 7 wherein the composition consists of 2-chloro-1,1,1,2-tetrafluoropropane and 2-chloro-3,3,3-trifluoropropene.

10. The method of claim 7 wherein the 2-chloro-1,1,1,2-tetrafluoropropane in present in an amount of from about 1 to about 25 weight percent.

11. The method of claim 7 wherein the 2-chloro-3,3,3-trifluoropropene is present in the amount from about 75 to about 99 weight percent.

12. The method of claim 7 wherein the composition has a boiling point of about 0° C. at a pressure of about 9 psia; or a boiling point of from about 25° C. at a pressure of about 24 psia; or a boiling point of about 60° C. at a pressure of about 65 psia.

13. A method for removing 2-chloro-3,3,3-trifluoropropene from a mixture containing 2-chloro-3,3,3-trifluoropropene and at least one impurity, which comprises adding 2-chloro-1,1,1,2-tetrafluoropropane to the mixture in an amount sufficient to form an azeotropic or azeotrope-like composition of the 2-chloro-3,3,3-trifluoropropene and the 2-chloro-1,1,1,2-tetrafluoropropane, and thereafter separating the azeotropic composition from the impurity.

14. The method of claim 13 wherein the impurity does not form an azeotropic mixture with 2-chloro-3,3,3-trifluoropropene or a mixture of 2-chloro-3,3,3-trifluoropropene and 2-chloro-1,1,1,2-tetrafluoropropane.

15. The method of claim 13 wherein the impurity does form an azeotropic mixture with 2-chloro-3,3,3-trifluoropropene, 2-chloro-1,1,1,2-tetrafluoropropane or a mixture of 2-chloro-3,3,3-trifluoropropene and 2-chloro-1,1,1,2-tetrafluoropropane.

16. The method of claim 13 wherein the impurity comprises a halocarbon.

17. The method of claim 13 wherein the impurity is miscible with 2-chloro-3,3,3-trifluoropropene.

18. The method of claim 13 wherein the impurity comprises one or more of 1,1,1,2,3-pentachloropropane; 1,1,2,3-tetrachloropropene; 2,3,3,3-tetrafluoropropene; comprises 2,3-dichloro-3,3-difluoropropene; 1,1,1,2,2-pentafluoropropane and 1,2-dichloro-3,3,3-trifluoropropene.

19. The method of claim 13 wherein the separating is conducted by distillation.

20. The method of claim 13 wherein the azeotropic composition consists essentially of from about 75 to about 99 weight percent 2-chloro-3,3,3-trifluoropropene and from about 1 to about 25 weight percent 2-chloro-1,1,1,2-tetrafluoropropane.

21. A method for removing 2-chloro-1,1,1,2-tetrafluoropropane from a mixture containing 2-chloro-1,1,1,2-tetrafluoropropane and at least one impurity, which comprises adding 2-chloro-3,3,3-trifluoropropene to the mixture in an amount sufficient to form an azeotropic or azeotrope-like composition of the 2-chloro-1,1,1,2-tetrafluoropropane and the 2-chloro-3,3,3-trifluoropropene, and thereafter separating the azeotropic composition from the impurity.

22. The method of claim 21 wherein the impurity does not form an azeotropic mixture with 2-chloro-1,1,1,2-tetrafluoropropane, 2-chloro-3,3,3-trifluoropropene or a mixture of 2-chloro-1,1,1,2-tetrafluoropropane and 2-chloro-3,3,3-trifluoropropene.

23. The method of claim 21 wherein the impurity does form an azeotropic mixture with 2-chloro-1,1,1,2-tetrafluoropropane, 2-chloro-3,3,3-trifluoropropene, or a mixture of 2-chloro-1,1,1,2-tetrafluoropropane and 2-chloro-3,3,3-trifluoropropene.

24. The method of claim 21 wherein the impurity comprises a halocarbon.

25. The method of claim 21 wherein the impurity is miscible with 2-chloro-1,1,1,2-tetrafluoropropane.

26. The method of claim 21 wherein the impurity comprises one or more of 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane; and 1,2-dichloro-3,3,3-trifluoropropene.

27. The method of claim 21 wherein the separating is conducted by distillation.

28. The method of claim 21 wherein the azeotropic composition consists essentially of from about 1 to about 25 weight percent 2-chloro-1,1,1,2-tetrafluoropropane and from about 75 to about 99 weight percent 2-chloro-3,3,3-trifluoropropene.

* * * * *